United States Patent [19]

McAleer et al.

[11] Patent Number: 5,708,247
[45] Date of Patent: Jan. 13, 1998

[54] DISPOSABLE GLUCOSE TEST STRIPS, AND METHODS AND COMPOSITIONS FOR MAKING SAME

[75] Inventors: Jerome F. McAleer, Wantage; David Scott, Witney; Geoff Hall, Inverness; Manuel Alvarez-Icaza, Inverness; Elliot V. Plotkin, Inverness, all of United Kingdom

[73] Assignee: Selfcare, Inc., Waltham, Mass.

[21] Appl. No.: 601,223

[22] Filed: Feb. 14, 1996

[51] Int. Cl.$^6$ .................................................. G01N 27/26
[52] U.S. Cl. ................ 204/403; 204/415; 204/418; 435/287.1; 435/289.1; 435/817; 435/4; 435/14
[58] Field of Search ................ 204/403, 415, 204/418; 435/288, 291, 817, 4, 14, 287.1, 289.1

[56] References Cited

U.S. PATENT DOCUMENTS

| | | | |
|---|---|---|---|
| 4,195,129 | 3/1980 | Fukui et al. | 435/182 |
| 4,418,148 | 11/1983 | Oberhardt | 435/179 |
| 4,655,880 | 4/1987 | Liu | 204/1 T |
| 4,876,205 | 10/1989 | Green et al. | 436/66 |
| 4,966,671 | 10/1990 | Nylander et al. | 204/153.14 |
| 5,120,420 | 6/1992 | Nankai et al. | 204/403 |
| 5,124,253 | 6/1992 | Foulds et al. | 435/21 |
| 5,126,034 | 6/1992 | Carter et al. | 204/403 |
| 5,141,868 | 8/1992 | Shanks et al. | 435/288 |
| 5,262,035 | 11/1993 | Gregg et al. | 204/403 |
| 5,264,106 | 11/1993 | McAleer et al. | 204/403 |
| 5,286,362 | 2/1994 | Hoenes et al. | 204/403 |
| 5,288,636 | 2/1994 | Pollman et al. | 435/288 |
| 5,378,628 | 1/1995 | Grätzel et al. | 435/288 |
| 5,437,999 | 8/1995 | Diebold et al. | 435/288 |
| 5,565,085 | 10/1996 | Ikeda et al. | 204/403 |
| 5,582,697 | 12/1996 | Ikeda et al. | 204/403 |
| 5,582,698 | 12/1996 | Flaherty et al. | 204/403 |

FOREIGN PATENT DOCUMENTS

| | | |
|---|---|---|
| 0127958 | 12/1984 | European Pat. Off. |
| 0170375 | 2/1986 | European Pat. Off. |
| 55-10581 | 1/1980 | Japan |
| 55-10583 | 1/1980 | Japan |
| 55-10584 | 1/1980 | Japan |
| 55-12406 | 9/1980 | Japan |
| 89/08713 | 9/1989 | WIPO |
| 9427140 | 11/1994 | WIPO |
| 9702847 | 1/1997 | WIPO |

*Primary Examiner*—Bruce F. Bell
*Attorney, Agent, or Firm*—Oppedahl & Larson

[57] ABSTRACT

An improved disposable glucose test strip for use in a test meter of the type which receives a disposable test strip and a sample of blood from a patient and performs an electrochemical analysis is made using a working formulation containing a filler, an enzyme effective to oxidize glucose, e.g., glucose oxidase, and a mediator effective to transfer electrons from the enzyme. The working formulation is printed over a conductive carbon base layer to form a working electrode. The filler, for example a silica filler, is selected to have a balance of hydrophobicity and hydrophilicity such that one drying it forms a two-dimensional network on the surface of the conductive base layer. The response of this test strip is essentially temperature independent over relevant temperature ranges and is substantially insensitive to the hematocrit of the patient.

34 Claims, 6 Drawing Sheets

DISPOSABLE GLUCOSE TEST STRIPS, AND METHODS AND COMPOSITIONS FOR MAKING SAME

BACKGROUND OF THE INVENTION

This application relates to disposable glucose test strips for use in electrochemical determinations of blood glucose, and to methods and compositions for use in making such strips.

Glucose monitoring is a fact of everyday life for diabetic individuals, and the accuracy of such monitoring can literally mean the difference between life and death. To accommodate a normal life style to the need for frequent monitoring of glucose levels, a number of glucose meters are now available which permit the individual to test the glucose level in a small amount of blood.

Many of these meters detect glucose in a blood sample electrochemically, by detecting the oxidation of blood glucose using an enzyme such as glucose oxidase provided as part of a disposable, single use electrode system. Examples of devices of this type are disclosed in European Patent No. 0 127 958, and U.S. Pat. Nos. 5,141,868, 5,286,362, 5,288,636, and 5,437,999 which are incorporated herein by reference.

In general, existing glucose test strips for use in electrochemical meters comprise a substrate, working and reference electrodes formed on the surface of the substrate, and a means for making connection between the electrodes and the meter. The working electrode is coated with an enzyme capable of oxidizing glucose, and a mediator compound which transfers electrons from the enzyme to the electrode resulting in a measurable current when glucose is present. Representative mediator compounds include ferricyanide, metallocene compounds such as ferrocene, quinones, phenazinium salts, redox indicator DCPIP, and imidazole-substituted osmium compounds.

Working electrodes of this type have been formulated in a number of ways. For example, mixtures of conductive carbon, glucose oxidase and a mediator have been formulated into a paste or ink and applied to a substrate. EP 0 127 958 and U.S. Pat. No. 5,286,362. In the case of disposable glucose strips, this application is done by screen printing in order to obtain the thin layers suitable for a small flat test strip. The use of screen printing, however, introduces problems to the operation of the electrode.

Unlike a thicker carbon paste electrode which remains fairly intact during the measurement, screen printed electrodes formed from carbon pastes or inks are prone to break up on contact with the sample. The consequences of this breakup are two-fold. Firstly, the components of the electrode formulation are released into solution. Once these components drift more than a diffusion length away from the underlying conductive layer, they no longer contribute toward the measurement, but in fact diminish the response by depleting inwardly-diffusing analyte. Secondly, the breakup of the screen printed electrode means that the effective electrode area is falling over time.

The combination of these two effects results in current transients which fall rapidly from an initial peak over the period of the measurement, and a high sensitivity to oxygen which quickly competes with the mediator for the enzyme. This fact is clearly demonstrated by the much lower currents measured in blood samples than in plasma samples or other aqueous media, and can result in erroneous readings. A further consequence is that the transients are often "lumpy" as the electrode breaks up in a chaotic manner. Lumpy transients either give rise to erroneous readings or rejected strips, neither of which are acceptable.

In addition to the potential for electrode breakup of screen-printed carbon-based electrodes, known electrodes used in disposable glucose test strips have been kinetically-controlled, i.e., the current depends on the rate of conversion of glucose by the enzyme. Because the response measured by the instrument represents a balance between the reaction of enzyme and mediator, enzyme and glucose and enzyme and oxygen, and because each of these reactions has its own dependence on temperature, the response of a kinetically-controlled test strip is very sensitive to the temperature of the sample. Substantial variation in the measured glucose value can therefore occur as a result of variations in sample handling.

Because of the importance of obtaining accurate glucose readings to the well-being of a patient using the meter and disposable test strips, it would be highly desirable to have a glucose test strip which did not suffer from these drawbacks, and which therefore provided a more consistent and reliable indication of actual blood glucose values, regardless of actual conditions. It is therefore an object of the present invention to provide disposable glucose test strips which are not prone to electrode breakup on contact with a sample.

It is a further object of this invention to provide glucose test strips which provide a glucose reading that is essentially independent of the hematocrit of the sample.

It is a further object of the present invention to provide glucose test strips which are substantially independent of temperature over a range between normal body temperature and room temperature.

It is a further object of the invention to provide test strips which provide a substantially flat current transient, without significant decay for periods of at least 10 seconds after the peak current level is obtained.

SUMMARY OF THE INVENTION

The present invention provides an improved disposable glucose test strip for use in a test meter of the type which receives a disposable test strip and a sample of blood from a patient and performs an electrochemical analysis of the amount of glucose in the sample. The test strip comprises:

(a) a substrate;

(b) a reference electrode;

(c) a working electrode; and (d) means for making an electrical connection between the reference and working electrode and a glucose test meter. The working electrode comprises a conductive base layer disposed on the substrate and a non-conductive coating disposed over the conductive base layer. The non-conductive coating comprises a filler which has both hydrophobic and hydrophilic surface regions, an enzyme effective to oxidize glucose, e.g., glucose oxidase, and a mediator effective to transfer electrons from the enzyme to the conductive base layer. The filler is selected to have a balance of hydrophobicity and hydrophilicity such that on drying it forms a two-dimensional network on the surface of the conductive base layer. Preferred filler are non-conductive silica fillers. The response of this test strip is dependent on the diffusion rate of glucose, not on the rate at which the enzyme can oxidize glucose, such that the performance of the test strip is essentially temperature independent over relevant temperature ranges. Further, the silica appears to form a two-dimensional network which excludes red blood cells, thus rendering the test strip substantially insensitive to the hematocrit of the patient.

DETAILED DESCRIPTION OF THE INVENTION

Figure 1A:
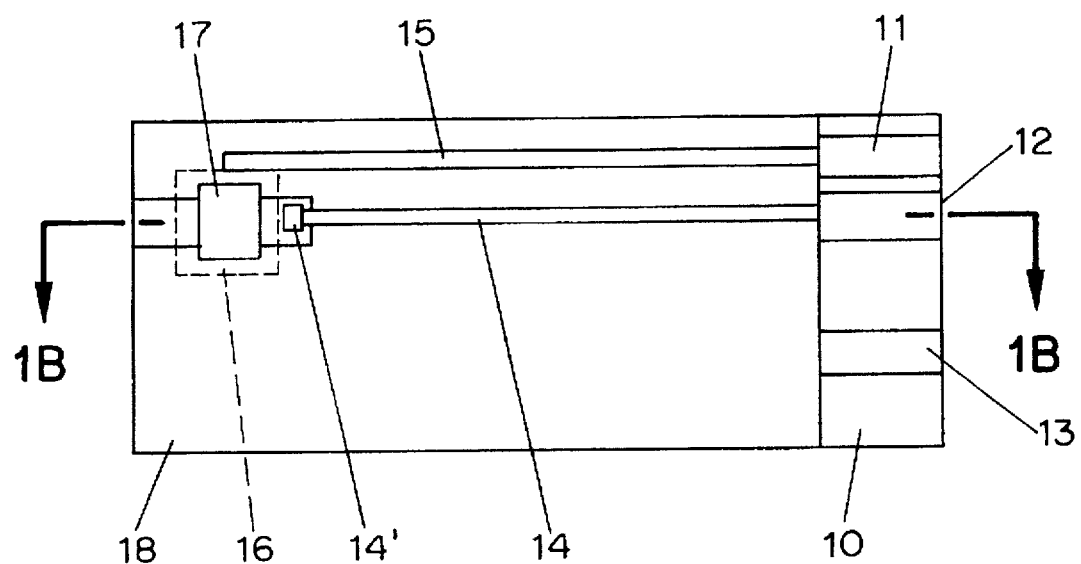
FIGS. 1A and 1B shows an electrode structure useful in a disposable test strip in accordance with the invention.
Figure 1B:
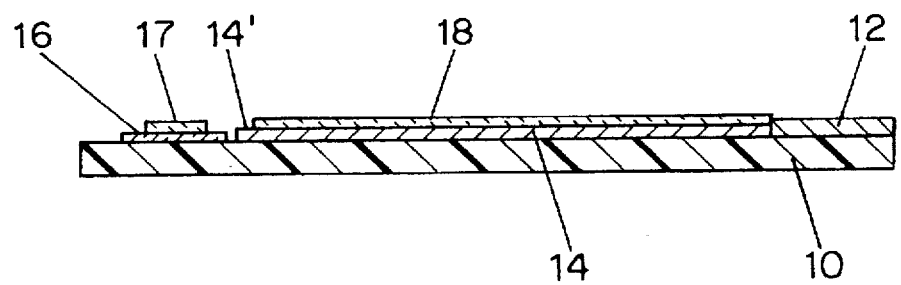

FIGS. 1A and 1B show electrodes useful in a disposable test strip in accordance with the invention. As shown, the electrodes are formed on a substrate 10. On the substrate 10 are placed a conductive base layer 16, a working electrode track 14, a reference electrode track 15, and conductive contacts 11, 12, and 13. An insulating mask 18 is then formed, leaving a portion of the conductive base layer 16, and the contacts 11, 12 and 13 exposed. A region of a working coating 17 is then applied over the insulating mask 18 to make contact with conductive base layer 16.

Figure 2:
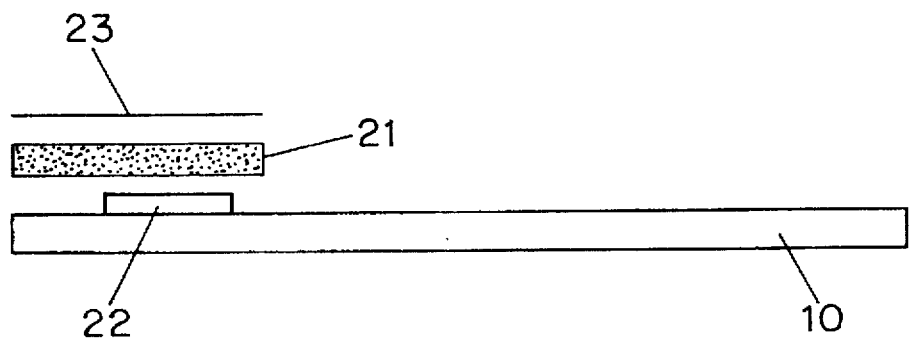
FIG. 2 shows a test strip in accordance with the invention.

The assembly shown in FIG. 1 provides a fully functional assembly for the measurement of blood glucose when connected to a meter. Advantageously, however, the electrode strips of the invention are finished by applying a polyester mesh 21 over the region of the working coating 17 of the electrode assembly 22, and then a top cover 23 to prevent splashing of the blood sample. (FIG. 2) The polyester mesh acts to guide the sample to the reference electrode, thereby triggering the device and initiating the test.

The substrate 10 used in making the test strips of the invention can be any non-conducting, dimensionally stable material suitable for insertion into a glucose test meter. Suitable materials include polyester films, for example a 330 micron polyester film, and other insulating substrate materials.

The working electrode track 15, the reference electrode track 14, and conductive contacts 11, and 12 can be formed from essentially any conductive material including silver, Ag/AgCl, gold, or platinum/carbon.

The conductive base layer 16 is preferably formed from conductive carbon. Preferred conductive carbon are ERCON ERC1, ERCON ERC2 and Acheson Carbon Electrodag 423. Carbon with these specifications is available from Ercon Inc. (Waltham, Mass., USA), or Acheson Colloids, (Princes Rock, Plymouth, England). The conductive base layer 16 makes contact with working electrode track 15, and is close too but not contacting the end of reference electrode track 15.

The insulating layer 18 can be formed from polyester-based printable dielectric materials such as ERCON R488-B(HV)-B2 Blue.

The key to the performance achieved using the present invention is in the nature of the coating 17. This coating contains a filler which has both hydrophobic and hydrophilic surface regions, an enzyme which can oxidize glucose, and a mediator which can transfer electrons from the enzyme to the underlying conductive base layer 16.

A preferred filler for use in the coating 17 is silica. Silica is available in a variety of grades and with a variety of surface modifications. While all silica compounds tested resulted in a product which could measure glucose under some conditions, the superior performance characteristics of glucose test strip of the invention are obtained when a silica having a surface modification to render it partially hydrophobic is used. Materials of this type include Cab-O-Sil TS610, a silica which is modified by partial surface treatment with methyl dichlorosilane; Cab-o-Sil 530, a silica which is modified by full surface treatment with hexamethyl disilazane; Spherisorb C4 silica, which is surface modified with 4 carbon chains; and other similarly modified by silicas, or combinations thereof. Silica with a surface modification which is too hydrophobic should be avoided, however, since it has been observed that C18-modified silica is too hydrophobic to form a printable ink.

During the process of manufacturing the ink of the invention, the particles are broken down by homogenization to expose hydrophilic inner portions of the silica particles. The actual particles present in the ink therefore have both hydrophilic and hydrophobic regions. The hydrophilic regions form hydrogen bonds with each other and with water.

When this material is formulated into an ink as described below in Example 1, and screen printed onto the conductive base layer 16, the dual nature of the material causes it to form layers of two-dimensional networks which take form as a kind of honeycomb. On rehydration, this layer does not break up, but swells forming a gelled reaction zone in the vicinity of the underlying conductive base layer 16. Enzyme, mediator and glucose move freely within this zone, but interfering species such as red blood cells containing oxygenated hemoglobin are excluded. This results in a device in which the amount of current generated in response to a given amount of glucose varies by less than 10 percent over a hematocrit range of 40 to 60%, and which is thus substantially insensitive to the hematocrit of the sample, and in fact performs substantially the same in blood as in a cell-free control solution. (FIGS. 3A–C, FIG. 4 and FIG. 5A–5C)

Figure 6A:
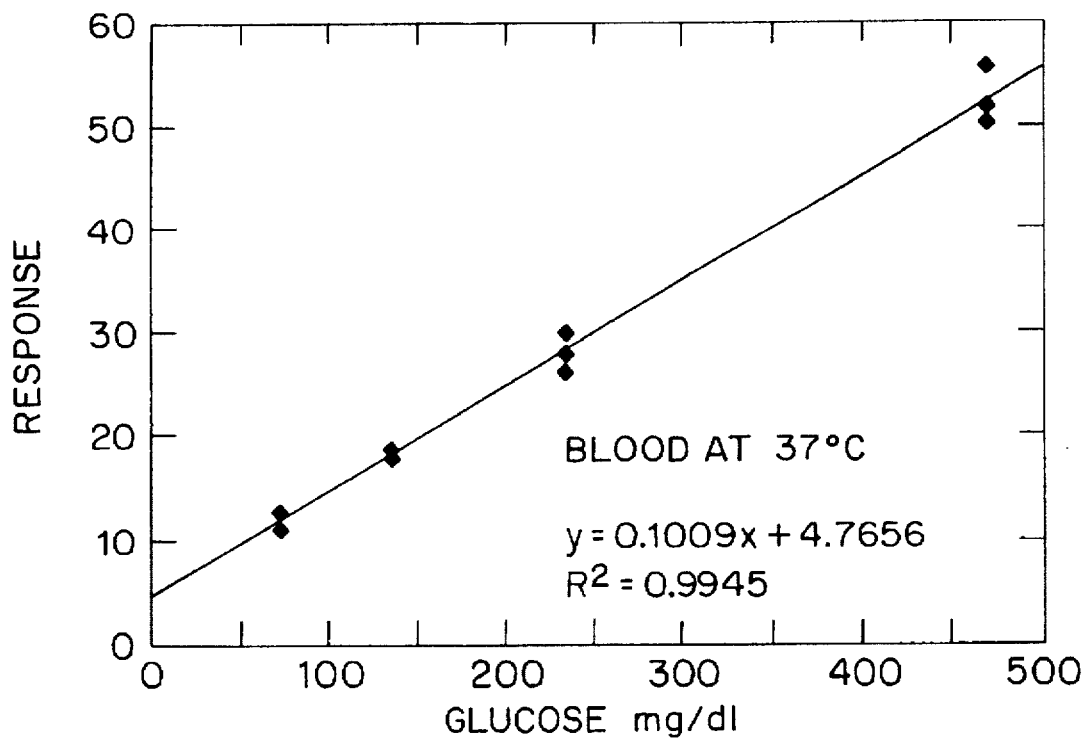
FIG. 6A and 6B show the current measured as a function of glucose at two different temperatures.
Figure 6B:
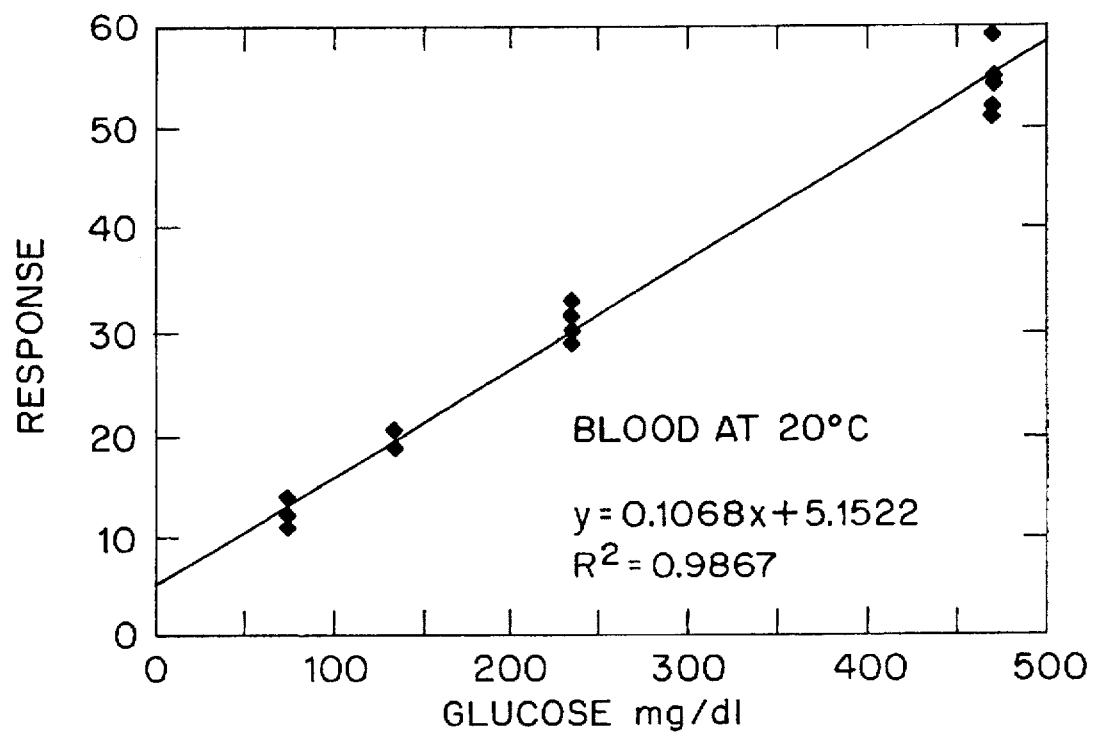

Furthermore, the gelled reaction zone presents a greater barrier to entry of glucose which makes the device diffusion, rather than kinetically limited. This leads to a device in which the measured current varies by less than 10 percent over a temperature range from 20° C. to 37° C. and which is thus essentially temperature independent. (FIGS. 6A and 6B)

The working layer is advantageously formed from an aqueous composition containing 2 to 10% by weight, preferably 4 to 10% and more preferably about 4.5% of a binder such as hydroxyethylcellulose or mixtures of hydroxyethylcellulose with alginate or other thickeners; 3 to 10% by weight, preferably 3 to 5% and more preferably about 4% silica; 8 to 20% by weight, preferably 14 to 18% and more preferably about 16% of a mediator such as ferricyanide; and 0.4 to 2% by weight, preferably 1 to 2% and more preferably about 1.6% of an enzyme such as glucose oxidase, assuming a specific activity of about 250 units/mg, or about 1000 to 5000 units per gram of ink formulation.

The working layer may also include additional ingredients without departing from the scope of the invention. For example, the nonconducting layer may include an antifoam. In addition, the nonconducting layer may be formulated with a buffering agent to control the pH of the reaction zone. The pH may be maintained at a level within the range from about pH 3 to pH 10. It is of particular utility to maintain the pH of the device at a level above 8 because at this pH oxygen bound to hemoglobin is not released. Further, at this pH, the reaction rate of glucose oxidase with oxygen is very low. Thus, selection of an appropriate pH can further stabilize the performance of the test strip against the effects of varying hematocrit.

Figure 7:
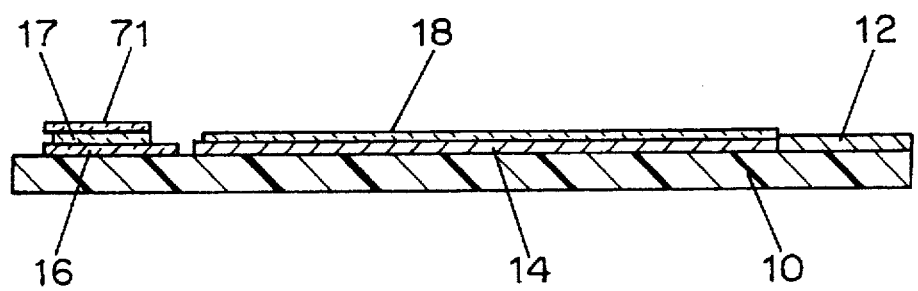
FIG. 7 shows a further embodiment of a glucose test strip according to the invention.

FIG. 7 shows an alternative embodiment of the invention. In this embodiment, a second working layer 71 is disposed over the first working layer 17. This layer is formed from a composition which is identical to the first working layer except that the enzyme or both the enzyme and the mediator are omitted. This layer further isolates the conductive base layer from contact with oxygen-carrying red blood cells, thus reducing the effects of oxygen. Furthermore, to the extent that enzyme may tend to diffuse away from the surface of the electrode during the course of the measurement, this layer provides an increased region in which it will have mediator available for the transfer of electrons.

EXAMPLE 1

A non-conducting formulation for preparation of the working layer 17 was made as follows. 100 ml of 20 mM aqueous trisodium citrate was adjusted to pH 6 by the addition of 0.1M citric acid. To this 6 g of hydroxyethyl cellulose (HEC) was added and mixed by homogenization. The mixture was allowed to stand overnight to allow air bubbles to disperse and then used as a stock solution for the formulation of the coating composition.

2 grams Cab-o-Sil TS610 silica and 0.1 grams of Dow Corning antifoam compound was gradually added by hand to 50 grams of the HEC solution until about ⅔ of the total amount has been added. The remainder is added with mixing by homogenization. The mixture is then cooled for ten minutes in a refrigerator. 8 g of potassium hexacyanoferrate (III) is then added and mixed until completely dissolved. Finally, 0.8 g of glucose oxidase enzyme preparation (250 Units/mg) is added and the thoroughly mixed into the solution. The resulting formulation is ready for printing, or can be stored with refrigeration.

EXAMPLE 2

To prepare glucose test strips using the ink formulation of Example 1, a series of patterns are used to screen print layers onto a 330 micron polyester substrate (Melinex 329). The first step is the printing of carbon pads. An array of 10×50 pads of carbon is formed on the surface of the polyester substrate by printing with EC2 carbon. (Ercon) The printed substrate is then passed through a heated dryer, and optionally cured at elevated temperature (e.g. 70° C.) for a period of 1 to 3 weeks.

Next, an array of silver/silver chloride connecting tracks and contacts is printed onto the substrate using ERCON R-414 (DPM-68)1.25 bioelectrode sensor coating material and dried. One working track which makes contact with the carbon pad and one reference track is printed for each carbon pad in the array.

A dielectric layer is then printed using ERCON R488-B (HV)-B2 Blue and dried. The dielectric layer is printed in a pattern which covers substantially all of each devices, leaving only the contacts, the tip of the reference electrode and the carbon pads uncovered.

On top of the dielectric layer the ink of Example 1 is used to form a working layer overlaid on top of each conductive carbon pad.

Polyester mesh strips (Scrynel PET230 HC) are then laid down across the substrate in lines, covering the reactions areas exposed by the windows in the dielectric. A 5 mm wide polyester strip (50 microns thick) is then applied over the top of the mesh strips, and the edges of the electrodes are heat sealed. Finally, the substrate is cut up to provide 50 individual electrodes, for example having a size of 5.5 mm wide and 30 mm long.

EXAMPLE 3

Figure 4:
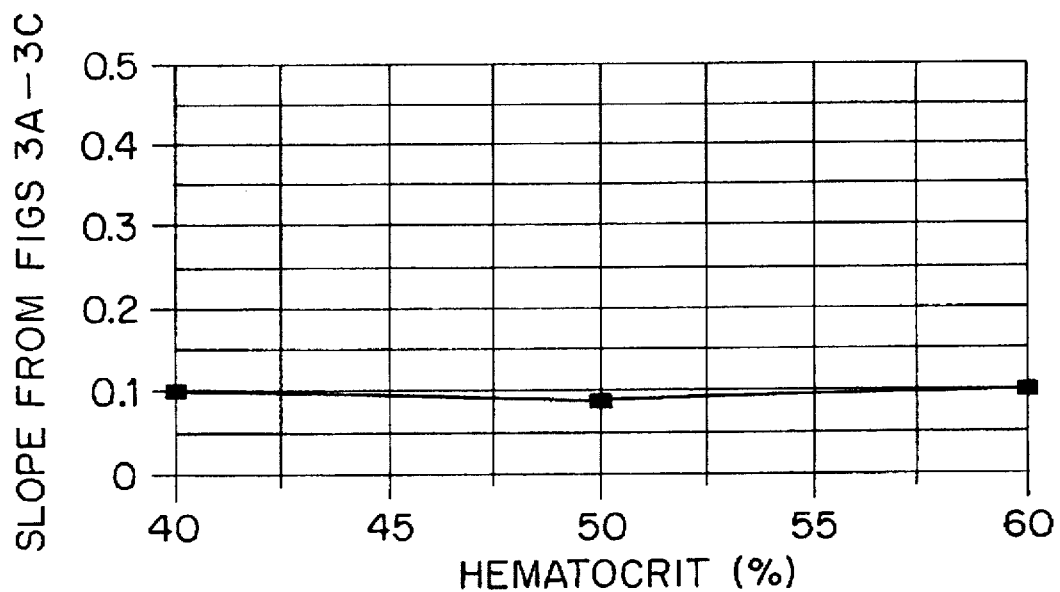
FIG. 4 shows the relationship of the glucose-concentration dependence of the measured current as a function of hematocrit.
Figure 3A:
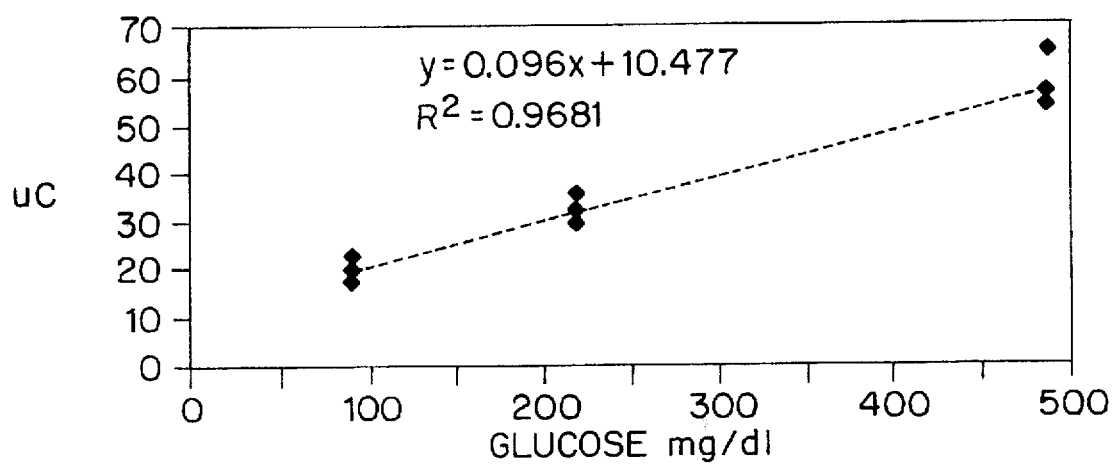
FIGS. 3A–3C show the current measured as a function of glucose concentration for three different hematocrit levels.
Figure 3B:
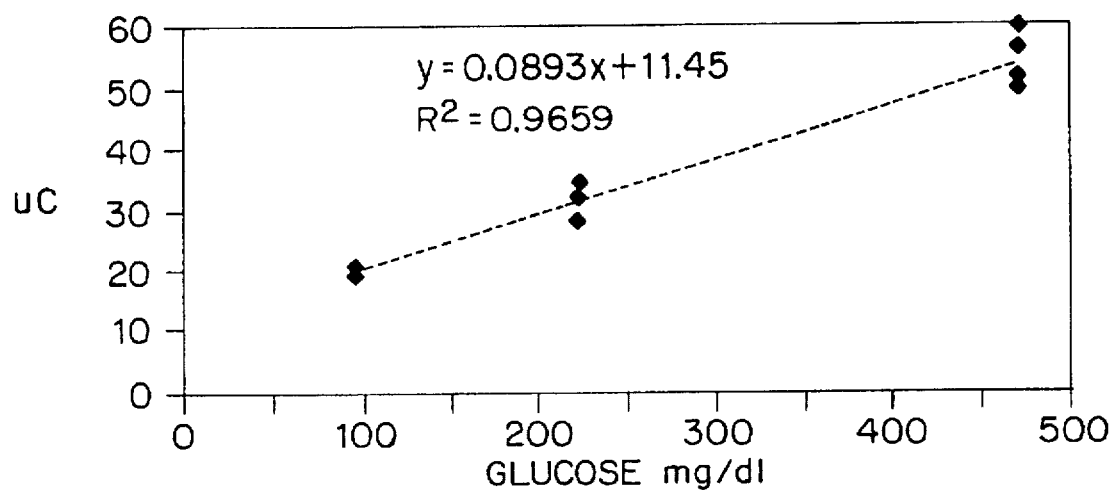
Figure 3C:
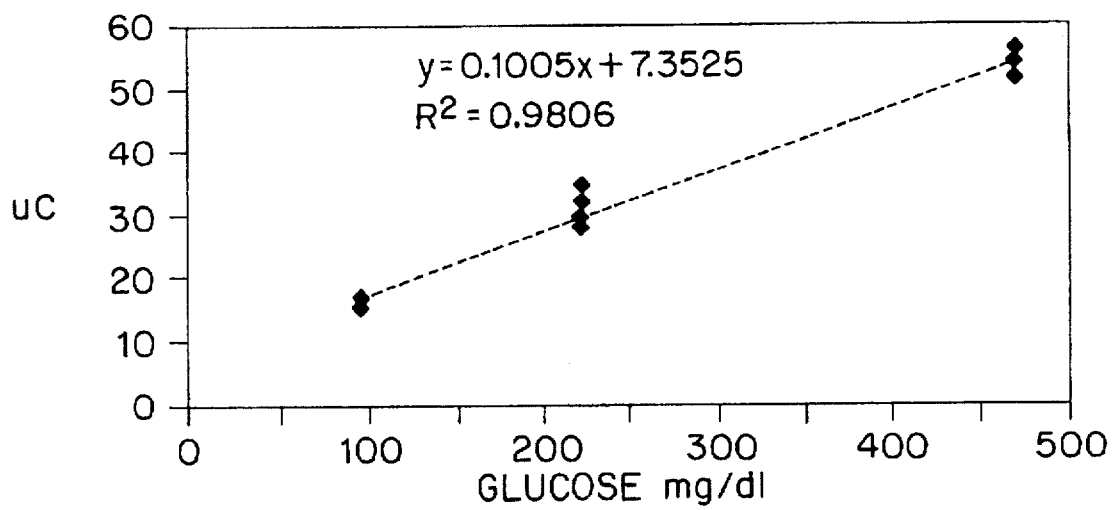

Test strips manufactured using the ink formulation of Example 1 in the manner described in Example 2 were placed in a test meter with an applied voltage of 500 mV and used to test blood samples having varying glucose concentrations and hematocrits ranging from 40% to 60%. FIGS. 3A–3C show the current measured 25 seconds after applying the voltage as a function of the glucose concentration, and FIG. 4 plots the slope of the glucose response as a function of hematocrit. As can be seen, the indicators produce highly reproducible current levels which are essentially independent of hematocrit.

EXAMPLE 4

Glucose test strips in accordance with the invention were made in accordance with Example 2, except the non-conductive layer was formed with 7 g Spherisorb C4 and 1 g Cab-o-Sil TS610. This formulation was laid down on two three different types of carbon-containing conductive base layers as follows:

A: Ercon EC1

B: Ercon EC2

C: Ercon EC2 on top of Acheson Carbon, Electrodag 423 SS.

Figure 5A:
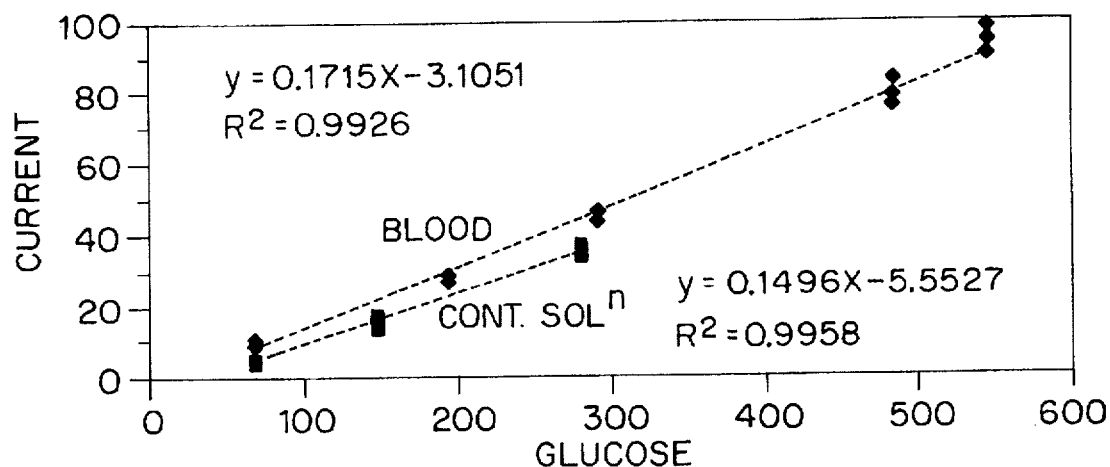
FIGS. 5A–5C show the current measured as a function of glucose in blood and a control solution for three different variations of the conductive base layer.
Figure 5B:
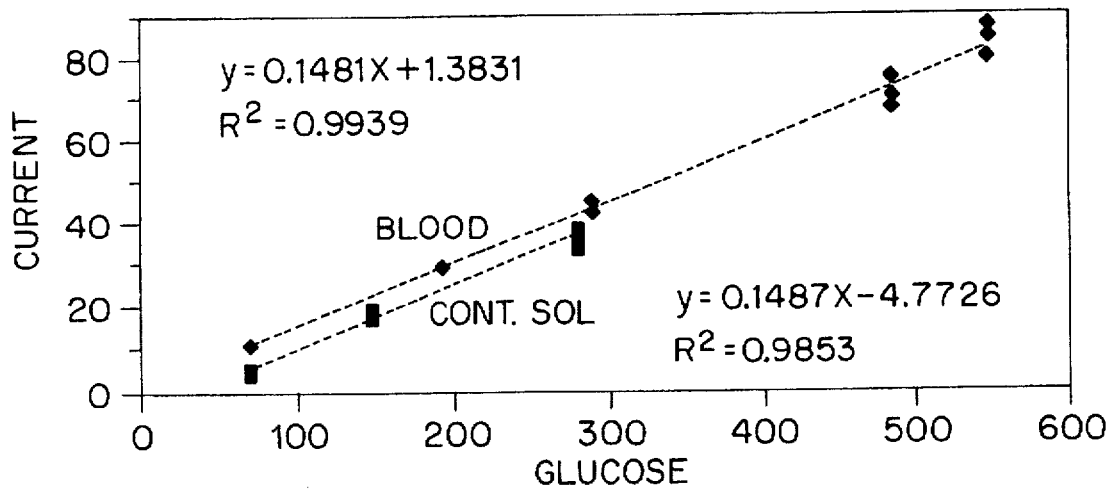
Figure 5C:
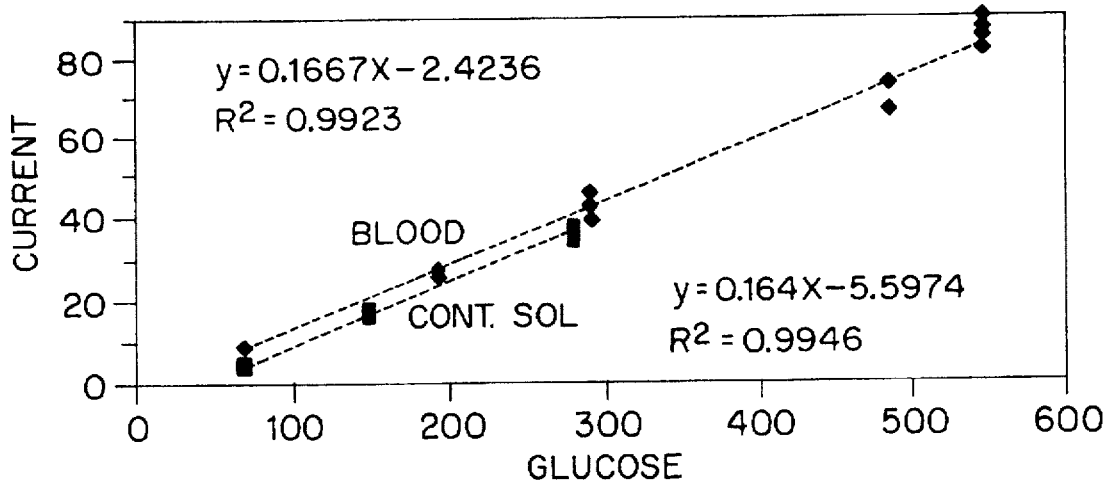

These test strips were used to measure varying levels of glucose in either a control solution (One Touch Control Solution, Lifescan Inc.) containing glucose in an inert solution or in blood at an applied voltage of 425 mV. The current observed 25 seconds after the voltage was applied was measured. FIGS. 5A–5C show the results obtained for the three formulations, A, B, and C, respectively. In all cases, the slope of the line showing the response of the meter to different glucose concentrations was essentially the same whether the measurement were made in blood or the control solution. Thus, this further demonstrates the independence of the test strips of the invention from the oxygen content and hematocrit of the sample, as well as the ability to use varied material as the conductive base layer.

EXAMPLE 5

Test strips prepared in accordance with Example 2 were tested at two different sample temperatures, namely 37° C. and 20° C. using an applied voltage of 425 mV. FIGS. 6A and 6B show the current measured 25 seconds after applying the voltage as a function of glucose concentration. As can be seen, the slopes of the two lines are essentially identical (0.1068 at 20° C. versus 0.1009 at 37° C.), thus demonstrating that the test strips provide essentially temperature-independent behavior over a temperature range from ambient to physiological temperatures.

EXAMPLE 6

Figure 8A:
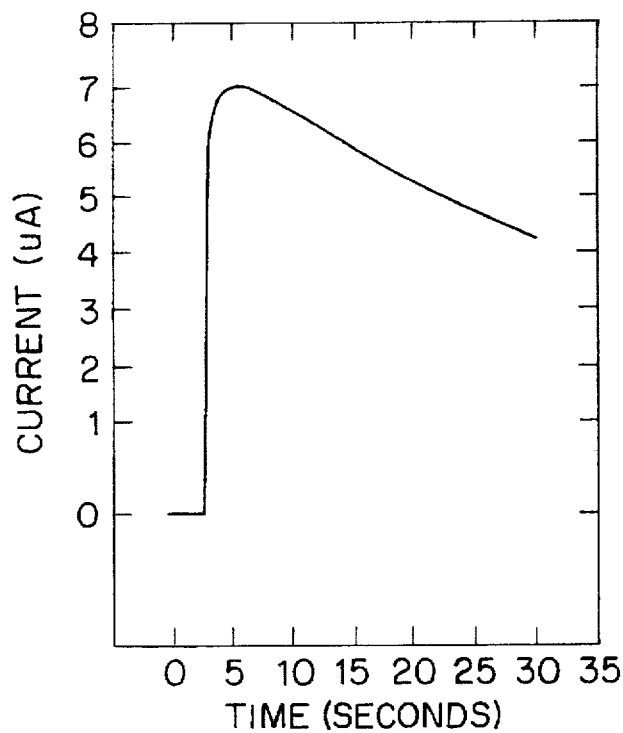
FIGS. 8A and 8B show a current transients observed using a test strip according to the invention and a commercial carbon-based test strip.
Figure 8B:
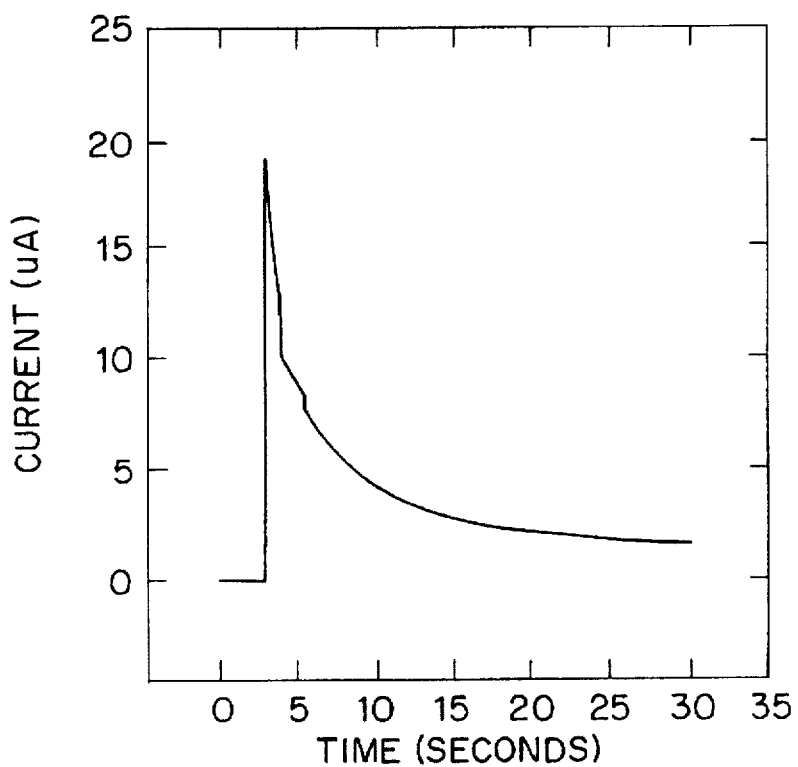

The current transient was measured for a test strip prepared in accordance with Example 2 and for a commercial test strip made with a carbon-containing ink. The results are shown in FIGS. 8A and 8B. As shown, the test strip of the invention (FIG. 8A) provides a very flat transient which maintains more than 50% of the peak current for a period of more than 25 seconds after the initial response from the test strip. In contrast, the carbon-based electrode exhibited an almost immediate decay in the current, having lost 50% of the peak current in a period of the first 1 to 2 seconds after the initial response from the test strip. This makes timing of the measurement difficult if peak current values are to be captured, or reduces the dynamic range of the meter is currents must be measrured after substantial decay has occurred. Thus, the test strips of the invention are advantageous in that they provide test strips in which the amount of current generated in response to a given amount of glucose decays by less than 50% in the 5 seconds following peak current generation.

We claim:

1. A disposable glucose test strip for use in a test meter of the type which receives a disposable test strip and a sample of blood from a patient and performs an electrochemical analysis of the amount of glucose in the sample, comprising:
   (a) a substrate;
   (b) a reference electrode;
   (c) a working electrode, said working electrode comprising a conductive base layer disposed on the substrate and a first working coating disposed over the conductive base layer, said first working coating comprising a filler having both hydrophobic and hydrophilic surface regions such that it forms a network upon drying, an enzyme effective to oxidize glucose, and a mediator effective to transfer electrons from the enzyme to the conductive base layer; and
   (d) means for making an electrical connection between the reference and working electrode and a glucose test meter.

2. The test strip of claim 1, wherein the working layer is non-conductive.

3. The test strip of claim 2, wherein the filler is silica.

4. The test strip of claim 3, wherein the conductive base layer comprises conductive carbon.

5. The test strip of claim 3, wherein the enzyme is glucose oxidase.

6. The test strip according to claim 3, wherein the mediator is ferricyanide.

7. The test strip of claim 3, wherein the first working layer is formed from an aqueous composition comprising weight 2 to 10% by weight of a binder 3 to 10% by weight of silica; 8 to 20% by weight of a mediator; and 1000 to 5000 units per gram of the aqueous composition of an enzyme for oxidizing glucose.

8. The test strip of claim 3, wherein the silica is a silica which has been modified by partial surface treatment with methyl dichlorosilane.

9. The test strip of claim 8, wherein the conductive base layer comprises conductive carbon.

10. The test strip of claim 8, wherein the enzyme is glucose oxidase.

11. The test strip of claim 8, wherein the mediator is ferricyanide.

12. The test strip of claim 8, wherein the first working layer is formed from an aqueous composition comprising weight 2 to 10% by weight of a binder 3 to 10% by weight of silica; 8 to 20% by weight of a mediator; and 1000 to 5000 units per gram of the aqueous composition of an enzyme for oxidizing glucose.

13. The test strip of claim 3, further comprising a second working layer comprising silica, a binder and a mediator but no glucose-oxidizing enzyme.

14. The test strip of claim 3, further comprising a second working layer comprising silica and a binder but no glucose-oxidizing enzyme.

15. The test strip of claim 1, further comprising a second working layer comprising a filler, a binder and a mediator but no glucose-oxidizing enzyme.

16. The test strip of claim 1, further comprising a second working layer comprising a filler and a binder but no glucose-oxidizing enzyme.

17. An aqueous composition comprising a binder, a silica filler having both hydrophobic and hydrophilic surface regions, at least one of an enzyme effective to oxidize glucose and an electron transfer mediator.

18. The composition of claim 17, wherein the filler is non-conductive.

19. An aqueous composition comprising 2 to 10% by weight of a binder; 3 to 10% by weight of silica; 8 to 20% by weight of a mediator; and 1000 to 5000 units per gram of the aqueous composition of an enzyme for oxidizing glucose.

20. The composition of claim 19, wherein the silica has both hydrophobic and hydrophilic surface regions.

21. The composition of claim 20, wherein the binder is hydroxyethylcellulose.

22. The composition of claim 19, wherein the enzyme is glucose oxidase.

23. The composition of claim 19, wherein the mediator is ferricyanide.

24. A method for making a disposable test strip for the electrochemical detection of glucose, comprising the steps of:
   (a) applying working and reference electrode tracks to a substrate;
   (b) applying a conductive base layer in contact with the working electrode track; and
   (c) applying a working layer over the conductive base layer, wherein the working layer comprising a filler having both hydrophobic and hydrophilic surface regions such that it forms a network upon drying, an enzyme effective to oxidize glucose, and a mediator effective to transfer electrons from the enzyme to the conductive base layer.

25. The method of claim 24, wherein the filler is non-conductive.

26. The method of claim 25, wherein the filler is silica.

27. The method of claim 26, wherein the conductive base layer comprises conductive carbon.

28. The method of claim 26, wherein the enzyme is glucose oxidase.

29. The method of claim 26, wherein the mediator is ferricyanide.

30. The method of claim 26, wherein the first working layer is formed from an aqueous composition comprising weight 2 to 10% by weight of a binder 3 to 10% by weight of silica; 8 to 20% by weight of a mediator; and 1000 to 5000 units per gram of the aqueous composition of an enzyme for oxidizing glucose.

31. The method of claim 30, wherein the silica is a silica which has been modified by partial surface treatment with methyl dichlorosilane.

32. A disposable glucose test strip comprising first and second electrodes which produce a current indicative of the amount of glucose in a sample applied to the strip in response to an applied voltage, wherein the amount of current generated by the electrodes in response to a given amount of glucose varies by less than 10 percent over a temperature range from 20° C. to 37° C.

33. A disposable glucose test strip comprising first and second electrodes which produce a current indicative of the amount of glucose in a sample applied to the strip in response to an applied voltage, wherein the amount of current generated by the electrodes in response to a given amount of glucose varies by less than 10 percent over a hematocrit range of 0 to 60%.

34. A disposable glucose test strip comprising first and second electrodes which produces a current indicative of the amount of glucose in a sample applied to the strip in response to an applied voltage, wherein the amount of current generated by the electrodes in response to a given amount of glucose decays by less than 50% in the 5 seconds following peak current generation.

* * * * *

UNITED STATES PATENT AND TRADEMARK OFFICE
CERTIFICATE OF CORRECTION

PATENT NO. : 5,708,247
DATED : January 13, 1998
INVENTOR(S) : McAleer et al.

Page 1 of 1

It is certified that error appears in the above-identified patent and that said Letters Patent is hereby corrected as shown below:

Column 3,
Line 33, delete "14" and insert -- 15 --; delete "15"and insert -- 14 --.
Line 67, delete "15" and insert -- 14 -- .

Column 6,
Line 26, after "concentration" insert --, for 60%, 50% and 40% hematocrit levels, respectively --.
Line 36, delete "on two" and insert -- onto --.

Column 10,
Line 4, delete "produces" and insert -- produce --.

Signed and Sealed this

Eleventh Day of September, 2001

*Attest:*

NICHOLAS P. GODICI
*Attesting Officer*     *Acting Director of the United States Patent and Trademark Office*

(12) EX PARTE REEXAMINATION CERTIFICATE (9917th)
United States Patent
McAleer et al.

(10) Number: US 5,708,247 C1
(45) Certificate Issued: Nov. 1, 2013

(54) DISPOSABLE GLUCOSE TEST STRIPS, AND METHODS AND COMPOSITIONS FOR MAKING SAME

(75) Inventors: Jerome F. McAleer, Wantage (GB); David Scott, Witney (GB); Geoff Hall, Inverness (GB); Manuel Alvarez-Icaza, Inverness (GB); Elliot V. Plotkin, Inverness (GB)

(73) Assignee: Lifescan Scotland Limited, Inverness (GB)

Reexamination Request:
No. 90/012,523, Sep. 12, 2012

Reexamination Certificate for:
Patent No.: 5,708,247
Issued: Jan. 13, 1998
Appl. No.: 08/601,223
Filed: Feb. 14, 1996

Certificate of Correction issued Sep. 11, 2001

(51) Int. Cl.
*C12Q 1/00* (2006.01)
*G01N 33/50* (2006.01)

(52) U.S. Cl.
USPC ............ 204/403.05; 204/403.11; 204/403.15; 204/415; 204/418; 435/14; 435/287.1; 435/289.1; 435/4; 435/817; 600/34

(58) Field of Classification Search
None
See application file for complete search history.

(56) References Cited

To view the complete listing of prior art documents cited during the proceeding for Reexamination Control Number 90/012,523, please refer to the USPTO's public Patent Application Information Retrieval (PAIR) system under the Display References tab.

*Primary Examiner* — Krisanne Jastrzab

(57) ABSTRACT

An improved disposable glucose test strip for use in a test meter of the type which receives a disposable test strip and a sample of blood from a patient and performs an electrochemical analysis is made using a working formulation containing a filler, an enzyme effective to oxidize glucose, e.g., glucose oxidase, and a mediator effective to transfer electrons from the enzyme. The working formulation is printed over a conductive carbon base layer to form a working electrode. The filler, for example a silica filler, is selected to have a balance of hydrophobicity and hydrophilicity such that one drying it forms a two-dimensional network on the surface of the conductive base layer. The response of this test strip is essentially temperature independent over relevant temperature ranges and is substantially insensitive to the hematocrit of the patient.

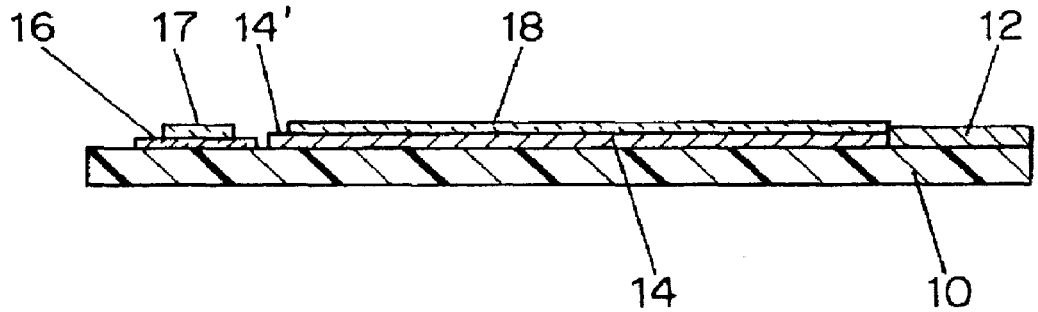

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-16, 24-32 and 34 is confirmed.

Claims 18 and 33 are cancelled.

Claims 17 and 19 are determined to be patentable as amended.

Claims 20-23, dependent on an amended claim, are determined to be patentable.

17. An aqueous composition comprising a binder, a silica filler having both hydrophobic and hydrophilic surface regions, [at least one of] an enzyme effective to oxidize glucose, and an electron transfer mediator, *wherein the aqueous composition is non-conductive*.

19. An aqueous composition comprising 2 to 10% by weight of a binder; 3 to 10% by weight of silica; 8 to 20% by weight of a mediator; and 1000 to 5000 units per gram of the aqueous composition of an enzyme for oxidizing glucose, *wherein the aqueous composition is non-conductive*.

* * * * *